United States Patent [19]

Noto et al.

[11] Patent Number: 5,079,173

[45] Date of Patent: Jan. 7, 1992

[54] METHODS, HYBRIDOMAS, MONOCLONAL ANTIBODIES AND SENSITIZED CELLS FOR MEASURING HBS ANTIGEN

[75] Inventors: Akira Noto; Akihiko Sato, both of Osaka; Kunihiro Nakajima, Nara, all of Japan

[73] Assignee: Shionogi & Co., Ltd., Osaka, Japan

[21] Appl. No.: 233,141

[22] Filed: Aug. 17, 1988

[30] Foreign Application Priority Data

Aug. 19, 1987 [JP] Japan .................. 62-205955

[51] Int. Cl.$^5$ .................. G01N 33/556; G01N 33/543; G01N 33/566
[52] U.S. Cl. .................. 436/521; 436/518; 436/501
[58] Field of Search .................. 436/521, 518, 501

[56] References Cited

U.S. PATENT DOCUMENTS

| | | | |
|---|---|---|---|
| 4,271,145 | 6/1981 | Wands et al. | 424/85 |
| 4,680,274 | 7/1987 | Sakai | 436/512 |

FOREIGN PATENT DOCUMENTS

| | | |
|---|---|---|
| 0027657 | 4/1981 | European Pat. Off. . |
| 0163312 | 12/1985 | European Pat. Off. . |
| 2419230 | 4/1973 | Fed. Rep. of Germany . |
| 58-127167 | 7/1983 | Japan . |
| 60-38656 | 2/1985 | Japan . |
| 62-10098 | 1/1987 | Japan . |
| 62-15464 | 1/1987 | Japan . |
| WO82/01072 | 4/1982 | PCT Int'l Appl. . |
| WO82/02661 | 8/1982 | PCT Int'l Appl. . |
| 1563839 | 4/1980 | United Kingdom . |

OTHER PUBLICATIONS

Roitt et al., "Immunology" Gower Publishing Co. (1977) p. 25.3.
Steinitz & Tamir, "The Coating of . . . ", J. Immuno. Methods, 76 (1985) 27–38.
Sasaki et al., "Passive Hemagglutination", J. Immuno. Methods 22:327–337 (1978).

*Primary Examiner*—Frederick E. Wallell
*Assistant Examiner*—Gregory Hook
*Attorney, Agent, or Firm*—Birch, Stewart, Kolasch & Birch

[57] ABSTRACT

This invention provides anti-HBs monoclonal antibodies HBs 8Cl, HBs 18E9 and HBs 22B7, an anti-human IgM monoclonal antibody HIgM 10C9 and an anti-mumps virus monoclonal antibody MPV 10G3 capable of inhibiting nonspecific reaction in the reverse passive agglutination, hybridomas producing them, a method for sensitizing fixed hemocytes with anti-HBs monoclonal antibodies, a fixed hemocyte sensitized with them by the said method, a method for inhibiting the said nonspecific reaction by utilizing the said monoclonal antibodies and an assay for HBs antigen by appropriately combining the above.

7 Claims, No Drawings

METHODS, HYBRIDOMAS, MONOCLONAL ANTIBODIES AND SENSITIZED CELLS FOR MEASURING HBS ANTIGEN

BACKGROUND OF THE INVENTION

1. Field of the Invention

This invention relates to anti-HBs monoclonal antibodies, a method for sensitizing fixed hemocytes with anti-HBs monoclonal antibodies, hemocytes sensitized with anti-HBs monoclonal antibodies, a method for measuring HBs antigen using anti-HBs monoclonal antibody-sensitized hemocytes, monoclonal antibodies for inhibiting non-specific reaction in measurement of HBs antigen and an inhibiting method thereby.

2. Prior Art

Hepatitis B is a disease caused by hepatitis B virus, which invades through a general infection route the blood. Babies are sometimes infected with this virus by mother-to-child transmission. About 90 percent of virus carriers are asymptomatic, but there is a risk of infection of others with this virus through the blood of the carriers, and the number of the carriers of this virus is estimated to be about 220 million in the world. In particular, the ratio of the carriers is high in Asia, and the number of patients in Japan is supposed to be about 1 million. Furthermore, hepatitis B has a high possibility of leading patients to more serious diseases such as liver cirrhosis and hepatocarcinoma.

In this situation, it is very important to discover and diagnose patients with hepatitis B and carriers of the virus, and also to detect hepatitis B virus in blood preparations. For this detection, along with the recent development of cell engineering technology, the hepatitis B surface antigen (abbreviated as HBs) in the specimen gets to be measured by using anti-HBs monoclonal antibody. Various types of anti-HBs monoclonal antibody have been obtained (for example, as disclosed in Japanese Kokai Nos. 56-73029, 62-10098, 57-501493, and 58-500300). And agglutinating reagents comprising erythrocytes sensitized with anti-HBs monoclonal antibody (for example, Japanese Kokai Nos. 58-127167 and 60-38656) and the measuring methods using them (for example, Japanese Kokai Nos. 57-501493 and 58-500300) have been developed. Furthermore, diagnosis kits using monoclonal antibodies to HBs are launched by some manufacturers.

In reverse passive agglutination reaction, nonspecific agglutinations may occur, and in order to inhibit them, the monoclonal antibody to other antigen than the antigen to be measured may be added in the reaction solution (as disclosed, for example, in Japanese Kokai No. 62-15464).

As the hemocytes used in the reverse passive agglutination reaction, fixed hemocytes of sheep or chicken are generally used, and sensitization of such hemocytes with monoclonal antibody was hitherto performed mainly in the presence of tannic acid.

So far, various anti-HBs monoclonal antibodies have been produced and various HBs measuring kits have been developed, but there has been a keen demand for those less in nonspecific reaction and higher in sensitivity.

SUMMARY

This invention provides anti-HBs monoclonal antibodies HBs 8C1, HBs 18E9 and HBs 22B7 which are useful in determining HBs antigen, an anti-human IgM monoclonal antibody HIgM 10C9 and an anti-mumps virus monoclonal antibody MPV 10G3 which are capable of inhibiting nonspecific reaction in the reverse passive agglutination and also provides hybridomas producing them. Further, this invention relates to a method for sensitizing fixed hemocytes with anti-HBs monoclonal antibodies in the presence of chromium chloride and to a fixed hemocyte sensitized with them according to the method, which give a highly sensitive assay for HBs antigen. Moreover, this invention provides a method for inhibiting nonspecific reaction in the reverse passive agglutination by utilizing the said monoclonal antibodies, which bring accuracy to the assay for HBs antigen. By appropriately combining the above, a highly sensitive and accurate assay for HBs antigen is realized.

In the conventional kits, since the nonspecific reactions often occurs, it is necessary to dilute the sample serum about 20 times beforehand. On the contrary, when measuring the HBs antigen according to the method of this invention, it is enough to dilute it about six times. So many times dilution of a sample serum causes an inaccuracy of the assay. Namely, assay for HBs antigen with high sensitivity and low non-specific reactivity is achieved by this invention.

DETAILED DESCRIPTION OF THE INVENTION

The monoclonal antibody of this invention may be prepared as follows by conventional procedure.

First, a desired antigen is administered to BALB/c or other strain of mouse, together with an adjuvant such as Freund's complete adjuvant for immunization and after the immunization, the spleen cells are taken out to be subjected to cell fusion as antibody-producing cells. The obtained mouse spleen cells are suspended in a culture medium, such as Eagle's MEM, Dulbecco's modified medium and RPMI 1640, containing about 10 to 20% of fetal calf serum (FCS), and after destroying the erythrocytes, the cells are fused with mouse myeloma cells having a proper marker, such as hypoxanthineguaninephosphoribosyl transferase deficiency (HGPRT$^-$) or thymidine kinase deficiency (TK$^-$). As a fusing agent, 50% polyethylene glycol (PEG) is added. The fused cells are suspended in hypoxathine-adenine-thymidine (HAT) medium, and are incubated while exchanging half portion of the HAT medium. After confirming formation of hybridoma the antibody titer in the culture supernatant can be measured by the passive hemagglutination (PHA) using hemocytes sensitized with said antigen. The hybridoma showing positive in the agglutination reaction is further cloned several times according to the limiting dilution method, thereby obtaining a hybridoma capable of producing the desired antibody steadily.

The desired monoclonal antibody is manufactured by increasing the obtained hybridoma in vitro or in vivo. In vitro, the cells are suspended in the generally employed culture medium as mentioned above, and are incubated for several days to obtain the desired antibody from the culture supernatant. In vivo, hybridoma is intraperitoneally inoculated in mouse or other mammals, and the ascites is taken out 10 to 20 days later, and the desired monoclonal antibody is obtained from the ascites.

From thus obtained culture supernatant or ascites, the desired monoclonal antibody is purified by combining the conventional methods, such as ammonium sulfate fractionation, DEAE Sepharose ion exchange column chromatography, hydroxy-apatite column chromatography, and protein A affinity column chromatography.

In this invention, according to the above method, various anti-HBs monoclonal antibodies were obtained. Among them, monoclonal antibodies HBs 22B7, 18E9 and 8C1 which are capable of presenting agglutination reagents with high sensitivity and little nonspecific reaction in measurement of HBs in the following manner were obtained. Meanwhile, as shown in the examples below, all anti-HBs monoclonal antibodies cannot present agglutination reagents low in nonspecific reactivity and high in sensitivity, and these monoclonal antibodies are useful in measuring HBs with particularly low nonspecific reactivity and high sensitivity.

Similarly, the anti-mumps virus monoclonal antibody MPV 10G3 and anti-human IGM monoclonal antibody obtained in this invention are particularly useful for inhibiting the nonspecific reaction in the following measurement of HBs.

Moreover, this invention also presents a method of sensitizing hemocytes with anti-HBs monoclonal antibody obtained by using HBs antigen as immunogen and a measuring method of HBs antigen by using thus sensitized hemocytes.

As hemocytes to be used in this invention, chicken hemocytes are preferable. Since chicken hemocytes are eucaryotes and the sedimentation rate is very fast as compared with that of cells of mammals, it is possible to make judgement in about 1 hour when chicken hemocytes are used as an agglutination reaction reagent, which is excellent in controllability as compared with the hemocytes of sheep or other mammals which requires 2 hour for operation. In measuring the HBs antigen in human serum, it is noteworthy that the human serum usually contains agglutination factors to foreign hemocytes (heteroagglutinins) which react nonspecifically with the agglutination reaction reagent. Chicken hemocytes, as compared with sheep or goose hemocytes, have low reactivity to heteroagglutinins contained in human serum, and are advantageous in view of low occurrence of nonspecific agglutination reaction which may result in false positive reaction.

The hemocytes to be used in this invention should preferably be fixed with glutaraldehyde or formalin in order to prevent hemolysis, and particularly glutaraldehyde is preferred since when fixed with formalin, the blood cells may agglutinate each other. The concentration of glutaraldehyde for fixing hemocytes is adjusted in proportion to the quantity of hemocytes. When using hemocytes at concentration of about 5%, the final concentration of glutaraldehyde is adjusted to 0.05 to 0.2%, and by reaction for 1 to 2 hours at room temperature, the fixation proceeds completely. When hemocytes at concentration of 10% are used, glutaraldehyde may be used in double for that when 5% hemocytes are used. However, if the hemocyte concentration is over 30%, nonspecific hemocyte agglutination occurs, and it is not recommended. To prepare stable fixed hemocytes free from clods of the hemocytes, it is enough for fixation to use hemocytes at concentration of about 5 to 7.5%. Even when the concentration of glutaraldehyde is less than 0.05%, fixation is possible if a longer reaction time is taken. But in order to achieve fixation simply in about 1 hour, a preferred concentration of glutaraldehyde is about 0.1%. If over 0.2%, meanwhile, fixation may be performed by shortening the reaction time, but since the fixation proceeds very fast and clods of agglutination are likely to be formed, it is difficult to uniformly prepare fixed hemocytes.

The sensitization of the obtained fixed hemocytes with monoclonal antibodies can be achieved by the chromium chloride method. In the conventional method using tannic acid, the absorption on $IgG_1$ class is particularly poor. However in the chromium chloride method the adsorption is better even for $IgG_{2a}$ or IgM as well as $IgG_1$. This sensitization is conducted in the presence of 5 to 1,000 μg/ml of monoclonal antibody and 5 to 600 μg/ml of chromium chloride for the fixed hemocytes at a concentration of 1 to 5%. Preferably, the sensitization is effected in the presence of 10 to 500 μg/ml of monoclonal antibody and 10 to 300 μg/ml of chromium chloride, for fixed hemocytes at a concentration of about 2.5%, and thereby sensitized hemocytes of high sensitivity may be obtained. When varying the concentration of fixed hemocytes, the concentration of monoclonal antibody and chromium chloride may be increased or decreased in proportion to the change of the concentration of fixed hemocytes. When being sensitized with two or more antibodies, the same operation may be repeated. In this specification, the concentration of fixed hemocytes is expressed in percentage (v/v) equivalent to hemocytes.

When the anti-HBs monoclonal antibody of IgM class is sensitized to hemocytes by the chromium chloride method mentioned above, an HBs antigen measurement reagent having a higher sensitivity than in conventional products can be obtained. However, IgM is generally high in sensitivity, but also high in nonspecific reactivity. To the contrary, IgG is not so high in the sensitivity as IgM, but higher in specificity. Accordingly, when the hemocytes sensitized with IgM are further sensitized with the anti-HBs monoclonal antibody of IgG class, a measurement reagent having higher sensitivity and low nonspecific reactivity than conventional products can be obtained. In order to decrease nonspecific reactions furthermore, it is preferable to use several types of hemocytes sensitized with both IgM and IgG by using several types of anti-HBs monoclonal antibody of IgG class. In this invention, a desired agglutination reagent was obtained by combining the hemocytes sensitized doubly with HBs 8C1 (IgG) and HBs 22B7 (IgM) and the hemocytes sensitized also doubly with HBs 18E9 (IgG) and HBs 22B7.

To decrease nonspecific reactions, moreover, the IgM used in sensitization may be added to the reaction solution after being denatured by glutaraldehyde or heat. Or when denatured or undenatured IgG and IgM that are different from those used in sensitization are added, nonspecific reactions are further inhibited. In this invention, by adding glutaraldehyde-denatured HBs 22B7 and also, as required, undenatured HIgM 10C9 and thermally denatured MPV 10G3 in the reaction solution, nonspecific reactions could be inhibited. The addition should be as much as possible as far as the reaction may not be impeded. And more practically when each of them is added by 1 to 300 μg/ml, a desired inhibitory effect against nonspecific reactions will be obtained.

Besides, when the above methods are combined, it is possible to measure the HBs antigen at an extremely high sensitivity and specificity.

EXAMPLE 1

Anti-HBs monoclonal antibody i. Preparation of immunogen (see Table 1)

HBs antigen-positive serum was salted out in 45% ammonium sulfate to sediment HBs antigen. (recovery 85%). This HBs antigen was dialyzed against 50 mM citrate buffer (pH 5.56) and applied to DEAE Sepharose CL-4B column equilibrated with the same buffer, and unadsorbed fractions were collected (yield 49%). Next, the HBs antigen fractions were applied to CM Sepharose CL-4B column equilibrated with 80 mM citrate buffer, and unadsorbed fractions were collected (recovery 37%). After dialyzing these fractions against PBS, they were passed through goat anti-human serum IgG Sepharose column for removing human serum components and pass-through fractions were collected as partially purified HBs antigen (recovery 30%) to be inoculated as the immunogen into BALB/c mouse.

TABLE 1

| | Preparation of Immunogen | | | | | | | |
|---|---|---|---|---|---|---|---|---|
| Refining Step | Volume ml | Protein mg/ml | Total protein mg | RPHA antibody titer | Unit activity PHA/mg/ml | Purification folds (times) | Protein recovery % | Antigen recovery % |
| Serum | 300 | 65.0 | 19,500 | 16,000 | 246 | 1 | | 100 |
| 45% Ammonium sulfate sedimentation | 100 | 30.0 | 3,000 | 40,960 | 1,365 | 5.5 | 15.4 | 85.3 |
| DEAE Sepharose | 197 | 7.5 | 1,478 | 12,000 | 1,600 | 6.5 | 7.6 | 49.3 |
| CM Sepharose | 345 | 3.3 | 1,139 | 5,120 | 1,551 | 6.3 | 5.8 | 36.8 |
| Anti-human Sepharose | 400 | 1.9 | 855 | 3,200 | 1,684 | 6.8 | 4.4 | 30.0 |

The protein content was measured by the method proposed by Lowry et al. (J. Biol. Chem. 193, 265-275, 1971). HBS antigen titer was measured by using RPHA reagent kit (Fuji Rebio, Serodia-HBs) using sheet erythrocytes sensitized with anti-HBs antibody.

ii. Preparation of mouse spleen cells

BALB/c mise were immunized by subcutaneous injection of partially-purified HBsAg (100 μg) with Freund's complete adjuvant, and thereafter only HBsAg (100 μg) was subcutaneously administered every 2 weeks for three to five times, and three days after the final immunization, spleen cell suspensions were prepared for cell fusion.

iii. Preparation of hybridoma

Mouse spleen cells and mouse myeloma cells SP2/0-Ag14 (SP2) were fused by the conventional method.

Mouse spleen cells were taken out, and were suspended in 10 ml of RPMI 1640 culture medium containing 15% fetal calf serum (FCS). After centrifugation (200×g, 5 minutes), the cells were treated with a proper amount of 0.17M ammonium chloride to destroy the contained erythrocytes and suspended in 5 ml of RPMI 1640 culture medium without FCS. SP2 cells suspended in 5 ml of the same culture medium without FCS were added by 1/5 of spleen cell amount, mixed well, and centrifuged (200×g, 5 minutes) to remove the RPMI medium. To the resultant 1 ml of 50% polyethyleneglycol 4,000 (mixed with the same volume of RPMI 1640 medium) preincubated at 37° C. was gradually added and stirred well to fuse cells. After the fusion, RPMI 1640 culture medium containing 15% FCS was gradually added, and the cells were washed by centrifugation (200×g, 5 minutes) to remove polyethylene glycol, suspended in HAT (hypoxathine aminopterin thymidine) culture medium, and were placed in a 96-well flat bottom microplate at a rate of about $5 \times 10^6$ spleen cells/200 μl per well. On day 4 or 5 after start of incubation, half of the HAT medium in each well was exchanged, and on day 9 to 13, colony formation of hybridoma was recognized. The HBs antibody titer of the supernatant was measured by PHA agglutination reagent (Eizai, PHA method Eizai kit). After diluting 25 μl of culture supernatant five times in 100 μl of physiological saline, 5 μl thereof was mixed with 50 μl of diluent attached to the kit and 25 μl of antigen sensitized hemocytes, and the well showing positive agglutination was regarded as that containing anti-HBs antibody-producing hybridoma.

The HBs antibody-producing hybridoma was cloned 3 times by the limiting dilution to obtain 26 strains of stable anti-HBs monoclonal antibody-producing hybridoma. The obtained hybridoma was suspended in 90% FCS and 10% dimethylsulfoxide, and was stored in −80° storage or liquid nitrogen.

iv. Preparation of monoclonal antibody

In BALB/c mice older than 8 weeks, 0.25 ml of pristane (2,6,10,14-tetramethyl-pentadecane) was intraperitoneally administered, and 3 to 14 days later, $1 \times 10^6$ cells (1 ml) of hybridoma suspended in PBS were intraperitoneally administered. The accumulated ascites was collected 10 to 20 days later. In the ascites, the PHA titers of anti-HBs monoclonal antibodies ranged from 40,000 to 5,120,000. The collecting volume of the ascites was 1 to 5 ml per BALB/c mouse.

v. Isotype of monoclonal antibody and subtype of HBs antigen recognized by the said monoclonal antibody The isotype of monoclonal antibodies produced by 26 types of isolated and established hybridoma was identified in the following manner.

The isotype of immunoglobulin was identified by Ouchterlony's double immunodiffusion method of the culture supernatant of HBs antibody-producing hybridoma and purified monoclonal antibody (mentioned below) against sheep anti-mouse immunoglobulins M, G, A, $G_1$, $G_{2a}$, $G_{2b}$, $G_3$, κ and λ chain sera in agarose gel. At this time, by reacting the culture supernatant with each antiserum at 1:1 ratio and by reacting the tenfold dilutions of the purified monoclonal antibody with each antiserum, a clear precipitation line was observed.

To determine the subtype of HBs antigen recognized by the monoclonal antibody, first by the Ouchterlony's double immunodiffusion method using HBs antigens with known subtypes (adr, adw, ayr, ayw), monoclonal antibodies for recognizing each antigen, that is, 22B7 (anti-a), 11F1 (anti-ar), 5A5 (anti-d) and 18E9 (anti-d) were obtained. By the RPHI method with chicken hemocytes sensitized with these monoclonal antibodies with known subtypes, the subtype of the HBs antigen recognized by each monoclonal antibody was determined. That is, after 2-fold diluting HBs antigen-positive serum (antigen titer 256) from 1:2 to 1:256, 25 μl of anti-HBs monoclonal antibody (antibody titer 1000) was added to each well, and neutralization reaction was performed for 1 hour at 37° C. To each well, 25 μl of anti-a (22B7), anti-ar (11F1), anti-d (5A5) or anti-d (18E9) antibody-sensitized chicken fixed hemocytes were added respectively, mixed, and let stand at room temperature for 40 to 60 minutes, and the agglutination was observed. When the agglutination reaction between HBs antigen and each monoclonal antibody-sensitized hemocyte was inhibited by 2 wells or more, the added monoclonal antibody was identified to recognize the same subtype as recognized by the monoclonal antibody used in sensitization.

vi. Purification of monoclonal antibody

The monoclonal antibody belonging to the immunoglobulin class $IgG_1$ was purified by the protein A-affinity chromatography.

The ascites was centrifuged, filtered through 0.45 μm membrane filter, and dialyzed against 100 mM phosphate buffer (pH 9.2). It was applied to protein A-Sepharose column equilibrated with same buffer, and the adsorbed $IgG_1$ was eluted with 0.1M acetic acid and 0.14M sodium chloride. Immediately a proper amount of 2M tris-hydrochloride buffer (pH 9.0) was added for neutralization, and it was dialyzed against PBS to obtain purified monoclonal antibody ($IgG_1$).

The monoclonal antibody of $IgG_{2a}$ class was, after centrifuging and filtering the ascites, dialyzed against 100 mM phosphate buffer (pH 8.2) and treated in the same manner as in $IgG_1$ to obtain purified monoclonal antibody.

The monoclonal antibody of IgM class was purified by the hydroxy apatite chromatography. After removing the insoluble matter by centrifuging and filtering the ascites, it was dialyzed against 0.1M phosphate buffer (pH 6.8) and adsorbed on the hydroxy apatite column equilibrated with the same buffer. The absorbed IgM was eluted by increasing the phosphate concentration stepwise (0.2 to 0.4M), and the eluate was passed through a Sephadex G-25 column equilibrated with PBS so that buffer was replaced with PBS. Thus, purified monoclonal antibody (IgM) was obtained.

vii. Measurement of isoelectric point

Of the above purified monoclonal antibodies, the isoelectric point was measured in 14 types.

The isoelectric point of the monoclonal antibody of IgG class was measured by the isoelectric focusing of thin layer polyacrylamide gel, and the isoelectric point of the monoclonal antibody of IgM class was measured by the isoelectric focusing of thin layer agarose.

(1) Isoelectric focusing of thin layer polyacrylamide gel. To the anode of Ampholine PAG plate (manufactured by LKB, pH 3.5 to 9.5), an electrode filter paper soaked in 1M phosphoric acid was set, and an electrode filter paper soaked in 1M sodium hydroxide was set to its cathode. On the plate, a sample applicator filter paper containing monoclonal antibody of IgG class was set. Electrophoresis was performed for 90 minutes at a constant electric power of 30 W and a temperature of 10° C. After the electrophoresis, the gel plate was dipped in a fixing solution*. And after letting stand for 60 minutes, the gel surface was rinsed in a decoloring solution* and stained in a staining solution* at for 10 minutes. The gel was transferred in the decoloring solution, and the excess staining solution was decolored. The gel was dipped in storing solution* for 60 minutes, and after drying at room temperature overnight, it was stored by covering with plastic sheet.

The isoelectric point of monoclonal antibody was determined on the basis of the moving distance of pI-known protein for calibration that was electrophoresed at the same time.

| *Fixing solution: | Methanol | 150 ml |
|---|---|---|
| | Distilled water | 350 ml |
| | Sulfosalicylic acid | 17.25 g |
| | Trichloroacetic acid | 57.5 g |
| Staining solution: | Coomassie Brilliant Blue R250 | 0.115 g |
| | Decoloring solution | 100 ml |
| Decoloring solution: | Ethanol | 500 ml |
| | Acetic acid | 160 ml |
| | Distilled water is added to make up 2 liters in whole. | |
| Storing solution: | Glycerine | 50 ml |
| | Decoloring solution | 500 ml |

(2) At the anode side of Ampholine agarose plate (manufactured by LKB, pH 3.5 to 9.5), an electrode filter paper soaked in 0.5M acetic acid was placed, and an electrode filter paper soaked in 0.5M sodium chloride was placed at the cathode side, and an applicator filter paper having monoclonal antibody was placed on the plate. Electrophoresis was performed for 30 minutes at a constant voltage by setting the initial voltage at 500 V (10° C.). After the electrophoresis, agarose gel was dipped in a fixing solution* for 10 minutes and then in ethanol for 10 minutes. The gel was dried by drier and dipped in staining solution* for 5 minutes. The excess staining solution was removed in a decoloring solution*. After decoloring, the gel was dried and stored.

The isoelectric point of the monoclonal antibody was determined on the basis of the moving distance of the pI-known protein for calibration that was electrophoresed at the same time.

| *Fixing solution: | Trichloroacetic acid | 100 g |
|---|---|---|
| | Sulfosalicylic acid | 10 g |
| | Distilled water | 1000 ml |
| Staining solution: | Coomassie Brilliant Blue R250 | 1.5 g |
| | Decoloring solution | 300 ml |
| Decoloring solution: | 95% ethanol | 350 ml |
| | Glacial acetic acid | 100 ml |
| | Distilled water is added to make up 1000 ml | |

The results are shown in Table 2.

TABLE 2

Properties of Monoclonal Antibodies

| Monoclonal antibody | Ig isotype | HBs subtype | Isoelectric point | Antibody titer of ascites |
|---|---|---|---|---|
| 2D9 | $IgG_1/\kappa$ | d | 5.7–5.8 | 2,560,000 |
| 5A5 | $IgG_{2a}/\kappa$ | d | 6.6–7.5 | 640,000 |
| 5A11 | $IgG_1/\kappa$ | d | 6.4–7.5 | 2,560,000 |
| 8C1 | $IgG_1/\kappa$ | d | 5.8–6.2 | 1,280,000 |
| 11A5 | $IgG_1/\kappa$ | d | 6.3–6.6 | 40,000 |
| 11B1 | $IgG_1/\kappa$ | d | — | 1,280,000 |
| 11B3 | $IgG_1/\kappa$ | a | 7.3–7.9 | 160,000 |
| 11B5 | $IgG_1/\kappa$ | r | — | 5,120,000 |
| 11B10 | $IgG_1/\kappa$ | a | 6.1–6.4 | 160,000 |
| 11C6 | $IgG_1/\kappa$ | — | 5.9–6.0 | 160,000 |
| 11C7 | $IgG_1/\kappa$ | a | — | 5,120,000 |
| 11E6 | $IgG_1/\kappa$ | d | — | 5,120,000 |
| 11F1 | $IgG_{2a}/\kappa$ | a, r | 6.2–6.6 | 1,280,000 |
| 11G12 | $IgG_1/\kappa$ | — | 6.1–6.5 | 80,000 |
| 12D5 | $IgG_1/\kappa$ | a | 6.3–6.9 | 40,000 |
| 12G12 | $IgG_1/\kappa$ | d | 6.3–6.5 | 80,000 |
| 16A3 | $IgG_1/\kappa$ | a | — | 80,000 |
| 16B4 | $IgG_1/\kappa$ | a | — | 320,000 |
| 17A6 | $IgG_1/\kappa$ | r | — | 1,280,000 |
| 18E9 | $IgG_1/\kappa$ | d | 5.7–5.8 | 2,560,000 |
| 22A12 | $IgG_1/\kappa$ | w | — | 640,000 |

TABLE 2-continued

| Monoclonal antibody | Properties of Monoclonal Antibodies | | | Antibody titer of ascites |
|---|---|---|---|---|
| | Ig isotype | HBs subtype | Isoelectric point | |
| 22B7 | IgM/κ | a | — | 320,000 |
| 22C4 | IgG$_1$/κ | — | 5.7-5.8 | 640,000 |
| 22H9 | IgG$_1$/κ | a | — | 640,000 |
| 23C7 | IgG$_1$/κ | a | — | 640,000 |
| 24B1 | IgG$_1$/κ | a | — | 80,000 | viii. Detection of HBs antigen by monoclonal antibody-sensitized hemocytes

Of the obtained monoclonal antibodies, the detection sensitivity of HBs antigen was measured on 12 types.

(1) Preparation of chicken fixed hemocytes. After centrifuging preserved chicken blood for 5 minutes at 600×g the supernatant was discarded and the rest was suspended in physiological saline. After centrifuging at 600×g for 5 minutes, the supernatant was discarded. After repeating this operation three times, the hemocytes were suspended in PBS at a concentration of 5% (v/v), and 1/10 portion of 1 to 1.2% (v/v, PBS) of glutaraldehyde was added. It was mixed slowly at room temperature for 1 to 2 hours for fixation. After that the hemocytes were centrifugally washed five times in distilled water (600×g, 5 minutes), and the concentration was adjusted to 5%. Then 0.1% portion of sodium azide was added, and the preparation was stored in a refrigerator.

(2) Preparation of monoclonal antibody-sensitized hemocytes. After washing 2 ml of fixed chicken hemocytes 5% (v/v) three times centrifugally with physiological saline (600×g, 5 minutes), 2 ml of physiological saline of anti-HBs monoclonal antibody (25 to 500 μg/ml) was equivalently mixed. Chromium chloride was added thereto by the final concentration of 25 to 200 μg/ml, gently stirred at room temperature for 2 hours. After the sensitization, the cells were centrifugally washed five times with 0.5% BSA/PBS (600×g, 5 minutes) and finally suspended in 0.5% BSA/PBS (16 ml) to obtain monoclonal antibody-sensitized hemocytes.

The HBs antigen-detection sensitivity of sensitized hemocytes is shown in Table 3.

Thus, when monoclonal antibodies HBs 18E9, HBs8Cl, HBs 22B7 were used, the detection sensitivity was highest and nonspecific reactions were few.

These anti-HBs antibody producing hybridomas have been deposited at ECACC (European Collection of Animal Cell Cultures), Porton Down, Salisbury, Wiltshire SP4 0JG, Great Britain, under the Budapest Treaty. The deposit numbers and dates are as follows.

| Hybridoma | Date | Number |
|---|---|---|
| HBs 22B7 | October 30, 1986 | 86103002 |
| HBs 18E9 | January 8, 1987 | 87010801 |
| HBs 8C1 | March 19, 1987 | 87031901 |

EXAMPLE 2

Anti-human IgM monoclonal antibody i. Preparation of immunogen

Preserved human serum (100 ml) was centrifuged (2000×g, 10 minutes) and filtered through 0.45 μm membrane filter. The resultant was dialyzed against 100 mM phosphate buffer (pH 6.8) and adsorbed on the hydroxy apatite column equilibrated with the same buffer. The adsorbed IgM was eluted by increasing phosphate concentration stepwise (0.2 to 0.4M) and the eluate was passed through Sephadex G-25 column equilibrated with PBS for replacing the buffer by PBS to obtain purified IgM.

TABLE 4

| | Purification of Human IgM | | | |
|---|---|---|---|---|
| Purification process | ml | Protein mg/ml | Total protein mg | Protein recovery % |
| Preserved serum | 100 | 58 | 58,000 | 100 |
| Hydroxy apatite chromatography | 42 | 2.2 | 92 | 0.16 |

The protein was measured by the method proposed by Lowry et al. (J. Biol. Chem., 193, 265-275, 1971).

ii. Preparation of human IgM-sensitized hemocytes

As the anti-human IgM antibody-detection reagent, the human IgM purified in step i was sensitized on fixed

TABLE 3

| No. | Monoclonal antibody | Monoclonal antibody μg/ml | HBs antigen detection sensitivity μg/ml | HBs antigen detection rate[*1] (%) | Incidence of nonspecific reaction[*2] |
|---|---|---|---|---|---|
| 1 | 2D9 | 500 | 4 | — | — |
| 2 | 5A5 | 500 | 4 | — | — |
| 3 | 5A11 | 500 | 16 | — | — |
| 4 | 8C1 | 500 | 4 | 90 | 0.5 |
| 5 | 11A5 | 500 | 16 | — | — |
| 6 | 11B3 | 500 | 8 | — | — |
| 7 | 11C6 | 500 | 8 | — | — |
| 8 | 11F1 | 500 | 4 | — | — |
| 9 | 11G12 | 500 | 16 | — | — |
| 10 | 12D5 | 500 | 16 | — | — |
| 11 | 18E9 | 500 | 8 | 90 | 0.5 |
| 12 | 22B7 | 250 | 2 | 100 | 50 |
| 13 | 8C1 (1) 22B7 (2) | 50 25 | 1 | 100 | 3.8 |
| 14 | 11F1 (1) 22B7 (2) | 100 25 | 1 | 100 | 50 |
| 15 | 18E9 (1) 22B7 (2) | 100 25 | 1 | 100 | 4.8 |
| 16 | 13 + 15 | (equivalently mixed) | 1 | 100 | 1.5 |

[*1] Detection rate on specimens judged to be positive by RIA method.
[*2] Incidence rate of nonspecific reactions on HBs antigen-negative specimens.

chicken hemocytes and the reagent for PHA method was thus prepared.

(1) Preparation of fixed chicken hemocytes.

After centrifuging preserved chicken blood at 600×g for 5 minutes, the supernatant was discarded and the rest was suspended in physiological saline. After repeating this operation three times, hemocytes were suspended in PBS at a concentration of 5 v/v %, and 1/10 portion of 1 to 1.2% (v/v PBS) glutaraldehyde was added and mixed slowly at room temperature for 1 to 2 hours. After that, the hemocytes were centrifugally washed five times with distilled water (600×g, 5 minutes), and the concentration was adjusted to 5 v/v %, and $NaN_3$ was added by 0.1%, and the preparation was stored in a refrigerator.

(2) Preparation of human IgM-sensitized fixed chicken hemocytes. Two ml of fixed chicken hemocytes (5 v/v %) was centrifugally washed twice with PBS (600×g, 5 minutes) to obtain 4 ml of the suspension in PBS. It was equivalently mixed with tannic acid (5 mg/dl) in PBS and tanned while slowly stirring for 10 minutes at 37° C. The tanned hemocytes were centrifugally washed twice with PBS (600×g, 5 minutes) to obtain 8 ml of the suspension in PBS. Purified human IgM (100 μg/ml PBS, pH 6.2) was equivalently added thereto and stirred for 2 hours at room temperature. In succession, 0.001% portion of glutaraldehyde was added, and further stirred for 1 hour at room temperature. By centrifugally washing five times with 0.5% BSA/PBS (600×g, 5 minutes), 16 ml of the suspension was obtained, and thus human IgM-sensitized hemocytes were prepared.

iii. Preparation of mouse spleen cells

BALB/c mice were immunized by subcutaneous injection of purified IgM (100 μg) with Freund's complete adjuvant, and thereafter only IgM (50 μg) was subcutaneously administered every 2 weeks for three to five times. Three days after the final immunization, spleen cell suspensions were prepared for cell fusion.

iv. Preparation of hybridoma

The mouse spleen cells were fused with mouse myeloma cells SP2/0-Ag14 (SP2) by the conventional method.

Mouse spleen cells were suspended in 10 ml of RPMI 1640 culture medium containing 15% FCS. After a centrifugal separation at 200×g for 5 minutes, the cells were treated with 0.17M $NH_4Cl$ to destroy the contained erythrocytes and suspended in 5 ml of RPMI 1640 culture medium free from FCS. The SP2 cells similarly suspended in 5 ml of culture medium free from FCS were added by 1/5 portion of the spleen cells prepared in the above method and mixed well. By a centrifugal separation at 200×g for 5 minutes, the RPMI 1640 medium was removed, and 1 ml of 50% polyethylene glycol 4,000 (equivalently mixed with RPMI 1640 medium) preincubated at 37° C. was gradually added and stirred well to fuse the cells. After the fusion, RPMI 1640 culture medium containing 15% FCS was gradually added, and the cells were centrifugally washed at 200×g for 5 minutes to remove polyethylene glycol. The resultant was suspended in HAT (hypoxanthine aminopterin thymidine) culture medium and placed in 96-well flat bottom microplate so that about $5 \times 10^6$ spleen cells/200 μl be present per well. On day 4 or 5 after start of incubation, half of the HAT medium of each well exchanged, and on day 9 to 13, colony formation of hybridoma was recognized. And the anti-IgM antibody titer of the culture supernatant was measured by the PHA agglutination reagent obtained in step ii.

After 20-fold diluting 10 μl of culture supernatant with 200 μl of PBS, 25 μl thereof was the mixed with 25 μl of human IgM-sensitized hemocytes, and the well showing agglutination was regarded to contain anti-human IgM antibody-producing hybridoma. The anti-human IgM antibody-producing hybridoma was cloned three times by the limiting dilution, and 5 strains of stable anti-human IgM monoclonal antibody-producing hybridoma were obtained. The obtained hybridomas were suspended in 90% FCS and 10% dimethyl sulfoxide and stored in −80° C. refrigerator or liquid nitrogen. One of the strains was named HIgM 10C9.

This anti-human IgM antibody producing hybridoma HIgM 10C9 has been deposited with ECACC (European Collection of Animal Cell Cultures), Porton Down, Salisbury, Wiltshire SP4 0JG, Great Britain, in terms of the Budapest Treaty, as the accession number 87031903 since Mar. 19, 1987.

v. Preparation of monoclonal antibody

In BALB/c mice older than 8 weeks, 0.25 ml of pristane (2,6,10,14-tetramethyl-pentadecane) was intraperitoneally administered, and 3 to 14 days later $1 \times 16^6$ cells (1 ml) hybridoma in PBS were intraperitoneally administered. On days 10 to 20 after the administration, the ascites was collected. In the ascites, anti-human IgM monoclonal antibody (the PHA titer 160,000 to 640,000) was contained. The sampling volume of the ascites was 1 to 5 ml per BALB/c mouse.

vi. Properties of the monoclonal antibody

Properties of the monoclonal antibody produced by the isolated and established hybridoma HIgM 10C9 are shown in Table 5.

The isotype of immunoglobulin was identified by the Ouchterlony's double immunodiffusion method of the culture supernatant of anti-human IgM antibody producing hybridoma against sheep anti-mouse immunoglobulins M, G, A, $G_1$, $G_{2a}$, $G_{2b}$, $G_3$, κ and λ chain sera in agarose gel.

The reactivity of the monoclonal antibody with immunoglobulins was checked by the PHA reagent comprising the purified human IgM, human IgG and human IgA (Cappel Products) sensitized to chicken fixed hemocytes by the tannic acid method (see ii. preparation of human IgM-sensitized hemocytes).

TABLE 5

| Immunoglobulin isotype | Reactivity with immunoglobulins* | | | Hemagglutination titer of ascites |
|---|---|---|---|---|
| | Human IgM | Human IgC | Human IgA | |
| IgM/κ | 500,000 | 1,000 or less | 1,000 or less | 160,000 to 640,000 |

*Hemagglutination titer of each PHA reagent.

Measurement of isoelectric point

The isoelectric point of monoclonal antibody was measured by the thin layer agarose isoelectric focusing.

At the anode side of Ampholine agarose plate (manufactured by LKB, pH 3.5 to 9.5), an electrode filter paper soaked in 0.5M acetic acid was placed, and at the cathode side an electrode filter paper soaked in 0.5M sodium chloride was placed, and an applicator filter paper having monoclonal antibody was put on the plate, and electrophoresis was performed at 10° C. for 30 minutes at constant voltage by setting the initial voltage at 500 V. After the electrophoresis, agarose gel was dipped in a fixing solution* for 10 minutes and then in ethanol for 10 minutes. The gel was dried by a drier and dipped in staining solution* for 5 minutes. The excess staining solution was removed with a decoloring solution*. After the decoloring, the gel was dried and stored.

The isoelectric point of the monoclonal antibody was determined on the basis of the moving distance of pI known protein for calibration that was electrophoresed at the same time.

| *Fixing solution: | Trichloroacetic acid | 100 g |
|---|---|---|
| | Sulfosalicylic acid | 10 g |
| | Distilled water | 1000 ml |
| Staining solution: | Coomassie brilliant blue R250 | 1.5 g |
| | Decoloring solution | 300 ml |
| Decoloring solution: | 95% ethanol | 350 ml |
| | Glacial acetic acid | 100 ml |
| | Distilled water is added to make up 1000 ml. | | vii. Purification of monoclonal antibody

The anti-human IgM monoclonal antibody HIgM 10C9 was purified by the hydroxy apatite chromatography. The ascites was centrifuged and filtered to remove an insoluble matter, and dialyzed against 0.1M phosphate buffer (pH 6.8). The resultant was adsorbed on the hydroxy apatite column equilibrated with the same buffer. The adsorbed IgM was eluted by increasing the concentration of phosphate stepwise (0.2 to 0.4M), and the eluate was passed through Sephadex G-25 column equilibrated with PBS for replacing the buffer with PBS. Thus a purified monoclonal antibody (IgM) was obtained.

EXAMPLE 3

Anti-mumps Virus Monoclonal Antibody i. Preparation of immunogen (1) Preparation of mumps crude HA antigen solution. Vero cells (Flow Laboratories Inc.) were inoculated with mumps virus (EXCH-2 strain), and produced HA antigen was purified to obtain HA antigen. Vero cells ($5 \times 10^7$) were placed in roller bottles with MEM (Eagle's minimum essential) medium containing 5% CS (calf serum) (0.3 rpm, 37° C.) to obtain single layer cultures. These Vero cells were infected with multiplicity of infection (M.O.I.) of 0.001 to 0.1 of mumps virus (EXCH-2 strain) and incubated for 5 to 7 days in MEM medium containing 2% CS. When CPE (cytopathic effect) was recognized as 100%, the cells were collected and suspended in PBS and ultrasonicated (10 kHz, 2.1 A, 10 minutes). The residue of cells was removed by a centrifugal separation (6000×g, 20 minutes), and the supernatant was recovered as a crude HA antigen solution.

(2) Inactivation of HA antigen

To the crude HA antigen solution, 1% Tween 80 aqueous solution was added by 1/7 portion and shaken vigorously for 5 minutes at room temperature. Then, ½ portion of diethyl ether was added thereto and was shaken vigorously for 15 minutes at 4° C. This solution was centrifuged at 1,600×g for 20 minutes, and the ether layer was removed by suction. A proper amount of nitrogen gas was passed through the water layer for removing the remaining ether to obtain an inactivated crude HA antigen solution.

(3) Preparation of fixed goose hemocytes

Preserved goose blood was centrifuged at 600 g for 5 minutes, and the supernatant was discarded. The rest was suspended in physiological saline and centrifugally washed at 600×g for 5 minutes. After repeating this operation three times, the hemocytes were suspended in PBS by 5 v/v %, and 1/10 portion of 1.2% glutaraldehyde (v/v PBS) was added. It was mixed slowly at room temperature for 1 to 2 hours. After the fixation the hemocytes were centrifugally washed five times with distilled water (600×g, 5 minutes). The concentration was adjusted to 10 v/v %, and 0.1% portion of $NaN_3$ was added. The preparation was stored in a refrigerator.

(4) Preparation of HA antigen. To the inactivated crude HA antigen solution, 100 ml of fixed goose hemocytes was added and stirred gently overnight at 4° C., thereby the HA antigen was adsorbed on hemocytes. After the unadsorbed protein was removed by centrifuging three times at 4° C. (600 g, 5 minutes), the hemocytes were suspended in 50 ml of PBS and let stand for 3 hours at 37° C. so that the HA antigen was desorbed from the hemocytes. The centrifugally separated supernatant was used as purified mumps virus HA antigen (HA titer 384, protein 420 μg/ml).

ii. Preparation of mumps virus HA antigen-sensitized hemocytes (1) Preparation of fixed chicken hemocytes. After preserved chicken blood was centrifuged at 600×g for 5 minutes, the supernatant was discarded and the rest was suspended in physiological saline and centrifuged at 600×g for 5 minutes, and the supernatant was removed. After repeating this operation for three times, the hemocytes were suspended in PBS at 5 v/v % concentration. To the suspension 1/10 portion of 1 to 1.2% (v/v PBS) of glutaraldehyde was added and slowly mixed at room temperature for 1 to 2 hours. After the fixation, hemocytes were centrifugally washed five times with distilled water (600×g, 5 minutes), and the concentration was adjusted to 5 v/v %. And then, 0.1% portion of $NaN_3$ was added thereto, and the preparation was stored in a refrigerator.

(2) Preparation of mumps virus HA antigen-sensitized fixed chicken hemocytes (PHA agglutination reagent). Two ml of fixed chicken hemocytes (5 v/v %) was centrifugally washed twice with PBS (600×g, 5 minutes) to obtain 4 ml of the suspension in PBS. The fixed hemocytes and tannic acid solution (5 mg/dl) in PBS were equivalently mixed and stirred gently for 10 minutes at 37° C. Thus tanned hemocytes were centrifugally washed twice with PBS (600×g, 5 minutes), and 8 ml of the suspension in PBS was obtained. Purified mumps virus HA antigen (100 μg/ml PBS, pH 6.2) was added, and was stirred for 2 hours at room temperature. After centrifugally washing five times with 0.5% BSA/PBS (600×g, 5 minutes), 16 ml of the suspension was obtained to be used as mumps virus HA antigen-sensitized hemocytes.

iii. Preparation of mouse spleen cells

BALB/c mice were immunized by subcutaneous injection of mumps virus antigen (HA 100 μg) with Freund's complete adjuvant. Only HA antigen (50 μg) was administered three to five times every two weeks, and three days after the final immunization, the spleen cell suspensions were prepared for cell fusion.

iv. Preparation of hybridoma

Mouse spleen cells and mouse myeloma cells SP 2/0-Ag14 (SP2) were fused by the conventional method. The mouse spleen cells were suspended in 10 ml of RPMI 1640 medium containing 15% FCS. After centrifugal separation for 5 minutes at 200×g, the cells were treated in a proper amount of 0.17M $NH_4Cl$ to destroy the erythrocytes contained therein. SP2 cells suspended in 5 ml of RPMI 1640 medium free from FCS were added by 1/5 portion of spleen cells and mixed well, and the RPMI 1640 medium was removed by centrifugation for 5 minutes at 200×g. To the resultant 1 ml of 50% polyethylene glycol 4000 preincubated at 37° C. (equivalently mixed with RPMI 1640 medium) was gradually added and mixed well to fuse the cells. After the fusion, RPMI 1640 medium containing 15% FCS was gradually added and centrifugally washed for 5 minutes at 200×g to remove polyethylene glycol. The resultant was suspended in HAT (hypoxanthine aminopterin thymidine) medium and placed in a 96-well flat bottom microplate so that about $5 \times 10^6$ spleen cells/200 μl be present in a well. On day 4 or 5 after start of incubation, half of HAT medium in each well was exchanged, and on day 9 to 13, formation of colonies of hybridoma was recognized. And the anti-mumps virus antibody titer in the culture supernatant was measured by the PHA agglutination reagent prepared in step ii. By adding 10 μl of culture supernatant to 100 μl of PBS containing 2% CS, it was diluted 11 times, and 25 μl thereof was mixed with 25 μl of mumps virus HA antigen-sensitized hemocytes. The well showing positive agglutination was regarded as containing anti-mumps virus antibody-producing hybridoma. The anti-mumps virus antibody-producing hybridoma was cloned three times by the limiting dilution to obtain 6 strains of stable anti-mumps virus monoclonal antibody-producing hybridomas. The obtained hybridomas were suspended in 90% FCS and 10% dimethyl sulfoxide and stored in −80° C. storage or liquid nitrogen. One of the strains was named MPV 10G3.

This anti-mumps virus antibody-producing hybridoma MPV 10G3 has been deposited with ECACC (European Collection of Animal Cell Cultures), Porton Down, Salisbury, Wiltsire SP4 0JG, Great Britain, in terms of the Budapest Treaty, as the accession number of 87031902 since Mar. 19, 1987.

v. Preparation of monoclonal antibody

In BALB/c mice older than 8 weeks, 0.25 ml of pristane (2,6,10,14-tetramethyl-pentadecane) was intraperitoneally administered, and 3 to 14 days later, $1 \times 10^6$ cells (1 ml) of hybridoma suspended in PBS were intraperitoneally administered. On days 10 to 20 after the administration, the accumulated ascites was collected. In the ascites anti-mumps virus monoclonal antibody of 250,000 PHA titer were contained. The collecting volume of the ascites was 1 to 5 ml per BALB/c mouse.

vi. Properties of monoclonal antibody

Properties of the isolated and established monoclonal antibody MPV 10G3 are shown in Table 6.

The isotype of immunoglobulin was identified by the Ouchterlony's double immunodiffusion method of the culture supernatant of anti-mumps virus antibody-producing hybridoma against sheep anti-mouse immunoglobulins M, G, A, $G_{2a}$, $G_{2b}$, $G_3$, anti-κ and λ sera in agarose gel.

TABLE 6

| Isotype | Isoelectric point | HI titer EXCH-2 | HI titer Enders strain | CF titer EXCH-2 | CF titer Enders strain |
|---|---|---|---|---|---|
| $IgG_1/\kappa$ | 7.5-7.8 | >5000 | 40 | <20 | <20 |

The monoclonal antibody reacted well with mumps virus EXCH-2 strain's HA antigen, but weekly with Enders strain's HA antigen. It did not react with mumps virus CF antigen.

Measurement of isoelectric point

The isoelectric point of monoclonal antibody was measured by the thin layer polyacrylamide gel isoelectric focusing.

Electrode filter papers soaked in 1M phosphoric acid and in 1M NaOH were respectively set at the anode and cathode of Ampholine PAG plate (manufactured by LKB, pH 3.5 to 9.5). On the plate, a sample applicator filter paper soaked with monoclonal antibody of IgG class was set, and electrophoresis was performed for 90 minutes at constant electric power of 30 W and temperature of 10° C. After the electrophoresis, the gel plate was dipped in a fixing solution* and let stand for 60 minutes. Then the gel surface was rinsed with a decoloring solution* and stained for 10 minutes at 60° C. in a staining solution*. The gel was transferred into a decoloring solution, and a excess staining solution was decolored. The gel was dipped in a storing solution for 60 minutes, and after drying overnight at room temperature, the preparation was stored by being covered with a plastic sheet.

The isoelectric point of the monoclonal antibody was determined on the basis of the moving distance of pI-known protein for calibration that was electrophoresed at the same time.

| *Fixing solution: | Methanol | 150 ml |
|---|---|---|
| | Distilled water | 350 ml |
| | Sulfosalicylic acid | 17.25 g |
| | Trichloroacetic acid | 57.5 g |
| Staining solution: | Coomassie Brilliant Blue R250 | 0.115 g |
| | Decoloring solution | 100 ml |
| Decoloring solution: | Ethanol | 500 ml |
| | Acetic acid | 160 ml |
| | Distilled water is added to make up 2 liters. | |
| Storing solution: | Glycerine | 50 ml |
| | Decoloring solution | 500 ml | vii. Purification of monoclonal antibody

The anti-mumps virus monoclonal antibody MPV 10G3 belonging to the immunoglobulin class $IgG_1$ was purified according to the protein A affinity chromatography. The ascites was centrifuged, filtered through 0.45 μm membrane filter, and dialyzed against 100 mM phosphate buffer (pH 9.2). It was applied to protein A-Sepharose column equilibrated with the same buffer, and the adsorbed $IgG_1$ was eluted with 0.1M acetic acid and 0.14M NaCl. Immediately, a proper amount of 2M Tris-hydrochloric acid buffer (pH 9.0) was added thereto for neutralization, and the resultant was dialyzed against PBS to obtain purified monoclonal antibody (IgG$_1$).

EXAMPLE 4

Preparation of Fixed Hemocytes

Preserved chicken blood was centrifugally washed three to five times in physiological saline (1,500 rpm, 5 minutes) so that serum components and leukocytes were removed. The obtained erythrocytes were suspended in PBS by about 7.5% (w/v). After adding 1.5% glutaraldehyde by 1/10 portion of the erythrocytes, it was mixed slowly at room temperature for 90 minutes by means of a stirrer. After centrifugally washing five times or more with distilled water (in the same conditions as above), the resultant was suspended by about 10% in distilled water containing 0.1% sodium azide. It was stored at 4° C. until antibody-sensitization. The fixed erythrocytes can be stored for about 2 years.

Aside from fixation with glutaraldehyde, it was attempted to fix erythrocytes with formalin, but they agglutinated each other after the fixation, and the erythrocytes could not be used.

Sensitization of Monoclonal Antibody to Fixed Hemocytes

With 5% fixed chicken centrifugally washed with 0.85% physiological saline (2,000 rpm, 5 minutes), 125 to 500 μg/ml of monoclonal antibodies HBs 11F1 (IgG$_{2a}$) were equivalently mixed. Furthermore, chromium chloride was added by 12.5 to 150 μg/ml, and the mixture was gently stirred for 2 hours at room temperature by means of a stirrer. After the reaction, the resultant was centrifugally washed five times with 0.5% BSA-PBS (2,000 rpm, 5 minutes) so that the unadsorbed antibodies were removed. Thus, antibody-sensitized hemocytes were prepared.

The results of measuring the minimum detection sensitivity of the obtained antibody-sensitized hemocytes to HBs antigen are shown below.

| Monoclonal antibody (μg/ml) | Chromium concentration (μg/ml) | Min. detection sensitivity (ng/ml) |
|---|---|---|
| 500 | 150 | 4 |
| | 100 | 4 |
| | 75 | 4 |
| 250 | 150 | 4 |
| | 100 | 4 |
| | 75 | 2 |
| | 50 | 2 |
| | 25 | 8 |
| | 12.5 | 16 |
| 125 | 150 | 2 |
| | 100 | 2 |
| | 75 | 2 |

Thus, in case of sensitizing hemocytes with monoclonal antibodies of IgG type, especially IgG$_{2a}$ type, 2.5% of fixed erythrocytes was sensitized with 50 to 250 μg/ml of monoclonal antibody in the presence of 50 to 150 μg/ml of chromium chloride to give sensitized hemocytes with high sensitivity and a little nonspecific reaction.

Similarly, fixed hemocytes are sensitized with HBs 22B7 (IgM), and the detection sensitivity was measured, of which results are shown below.

| Chromium chloride (μg/ml) | Monoclonal antibody (μg/ml) | Min. detection sensitivity (ng/ml) |
|---|---|---|
| 100 | 125 | 1 |
| | 63 | 1 |
| 50 | 250 | 1 |
| | 125 | 1 |
| | 63 | 1 |
| | 31 | 2 |
| 25 | 250 | 1 |
| | 125 | 1 |
| | 63 | 1 |
| | 31 | 2 |
| 13 | 250 | 2 |
| | 125 | 4 |
| | 63 | 2 |
| | 31 | 2 |

In this way, even from the monoclonal antibody of IgM type, sensitized hemocytes of high sensitivity could be prepared by the chromium chloride method.

Thus, by sensitizing 2.5% fixed hemocytes with 10 to 500 μg/ml of monoclonal antibody in the presence of 10 to 300 μg/ml of chromium chloride, sensitized hemocytes of high sensitivity can be prepared.

Comparison with tannic acid method

Monoclonal antibodies HBs 18E9 (IgG$_1$), HBs 11F1 (IgG$_{2a}$) and HBs 22B7 (IgM) were applied to sensitization by tannic acid method. After centrifugally washing 5% fixed chicken hemocytes twice with PBS (2,000 rpm, 5 minutes), 5 mg/ml tannic acid was equivalently mixed therewith and allowed to react in water bath of 37° C. for 10 minutes. After washing twice with PBS, the product was suspended in PBS (pH 6.4) at a concentration of 2.5% and equivalently mixed with 100 μg/ml monoclonal antibody. By mixing slowly at room temperature for 2 hours by means of a stirrer, monoclonal antibodies were adsorbed on hemocytes. The unadsorbed antibody was removed by centrifugal washing to obtain antibody-sensitized hemocytes. Between thus obtained antibody-sensitized hemocytes by the tannic acid method and the antibody-sensitized hemocytes by the above chromium chloride method (chromium chloride concentration 100 μg/ml, antibody concentration 200 μg/ml), minimum detection sensitivity of HBs antigen was compared.

| Monoclonal antibody | Minimum detection concentration (ng/ml) | |
|---|---|---|
| | Tannic acid method | Chromium chloride method |
| 18E9 (IgG$_1$) | 100 | 4 |
| 11F1 (IgG$_{2a}$) | 30 | 4 |
| 22B7 (IgM) | 30 | 2 |

As clear from the results shown above, in sensitizing the fixed hemocytes with monoclonal antibody, antibody-sensitized hemocytes of higher sensitivity were obtained by the chromium chloride method than by the conventional tannic acid method.

Inhibition of nonspecific reaction

Fixed chicken hemocytes at 5% were equivalently mixed with 100 μg/ml of anti-HBs monoclonal IgG (HBs 8Cl or HBs 18E9) in 100 μg/ml of chromium chloride, and allowed to react with each other for 1 hour at room temperature to sensitize the hemocytes with the antibody. Furthermore, chromium chloride and anti-HBs monoclonal IgM (HBs 22B7) were respectively added thereto by 25 µg/ml and 20 µg/ml and allowed to react for an hour. These hemocytes were centrifugally washed five times with 0.5% BSA-PBS (2,000 rpm, 5 minutes) and suspended at 0.5%. Anti-HBs monoclonal antibody-sensitized hemocytes were thus obtained.

For testing, 180 serum samples were prepared (HBs antigen negative, as tested by a commercial R-PHA reagent). To each well of microplates were added 25 µl of 0.25% BSA-PBS, 5 µl of the above serum and furthermore 50 µl of the sensitized hemocytes prepared above. The agglutination was observed one hour later. As a result, complete agglutination was noted in 88 out of 180 samples and weak agglutination in 42 samples, which indicated that the nonspecific reaction was considerably occurred therein.

The monoclonal IgM (HBs 22B7) used in the sensitization was denatured by glutaraldehyde and added to the 0.25% BSA-PBS by 10 to 100 µg/ml. On the same 180 samples, occurrence of nonspecific reaction was similarly investigated, and the number of samples with nonspecific reaction reduced from 88 to 39.

Furthermore, when monoclonal IgM to human IgM (HIgM 10C9) which could not bind with HBs antigen was added by 10 to 100 µg/ml, the nonspecific reaction decreased to 23 samples.

In succession, when heat-treated (60° C., 30 minutes) anti-mumps virus monoclonal antibody MPV 10G3 (IgG$_1$) was added by 10 to 100 µg/ml, the number of samples showing apparent nonspecific reaction decreased from 23 to 13.

Since monoclonal IgM (HBs 22B7) has anti-HBs antibody activity, when it is directly added, HBs antigen is neutralized, and the sensitivity of the kit is lowered. It is hence necessary to be added after being denatured for getting rid of antibody activity. As the methods of denaturing, glutaraldehyde treatment, 2-mercaptoethanol treatment, and heating (65° C.) method were employed. Above all, when denatured by treating with glutaraldehyde at a concentration of 0.01 to 0.1%, the anti-HBs antibody activity was lost or lowered, and the nonspecific reaction-inhibitory effect was also obtained. In the other methods, the 2-mercaptoethanol and heating treatments, the nonspecific reaction-inhibitory effect was lost as well as the antibody activity, and they were not effective methods.

As for the IgG$_1$ (MPV 10G3) to be added in the reaction solution, the thermally denatured material and undenatured material were compared. As for the nonspecific reaction to rheumatoid factor positive samples, the thermally denatured material indicated a greater inhibitory effect to the nonspecific reaction.

Measurement of HBs antigen

Fixed chicken hemocytes at 5% were equivalently mixed with 100 µg/ml of anti-HBs monoclonal IgG (HBs 8Cl or HBs 18E9) in the presence of 100 µg/ml of chromium chloride, and they were allowed to react at room temperature for 1 hour so that the antibody was sensitized to hemocytes. Furthermore, after adding 25 µg/ml of chromium chloride and 20 µg/ml of anti-HBs monoclonal IgM (22B7), the reaction was continued for another one hour. These hemocytes were centrifugally washed five times with 0.5% BSA-PBS and suspended by 0.5%, and HBs 8Cl- and HBs 22B7-sensitized hemocytes and HBs 18E9- and HBs 22B7-sensitized hemocytes were obtained.

To 0.25% BSA-PBS, the monoclonal antibody HBs 22B7 used in the above sensitization being denatured by glutaraldehyde, and monoclonal antibody HIgM 10C9 were respectively added by 25 µg/ml, and then the thermally denatured monoclonal antibody MPV 10G3 was added by 50 µg/ml.

The above reaction solution was transferred by 25 µl onto microplate, and 5 µl of sample was added thereto. Furthermore, 50 µl of 8Cl/22B7-sensitized hemocytes, 50 µl of 18E9/22B7-sensitized hemocytes, or 50 µl of equivalent mixture of 8Cl/22B7-sensitized hemocytes and 18E9/22B7-sensitized hemocytes were added, and the agglutination image was observed one hour later. The results are shown below.

| Monoclonal antibody-sensitized hemocytes | HBs antigen detection rate | Occurrence of non-/specific reaction |
|---|---|---|
| 8Cl/22B7 | 100% | 3.8% |
| 18E9/22B7 | 100% | 4.8% |
| 8Cl/22B7 + 18E9/22B7 | 100% | 1.5% |

Thus, in any case, favorable sensitivity was obtained, and nonspecific reactions were few, but when two different sensitized hemocytes were used, the nonspecific reactions were further inhibited. Therefore, the combination of 8Cl/22B7 and 18E9/22B7 produced the best result.

What we claim is:

1. Sensitized fixed hemocytes which are prepared by a process which comprises sensitizing fixed hemocytes with anti-HBs monoclonal IgM HBs 22B7 and anti-HBs monoclonal IgG HBs 8Cl or HBs 18E9 in the presence of chromium chloride.

2. The sensitized fixed hemocytes of claim 1, which are sensitized at a concentration of 1 to 5% with 5 to 1,000 µg/ml of said anti-HBs monoclonal antibody in the presence of 5 to 600 µg/ml of chromium chloride.

3. The sensitized fixed hemocytes of claim 1, wherein said fixed hemocytes are chicken erythrocytes fixed with glutaraldehyde.

4. A method which comprises inhibiting nonspecific reaction in a reverse passive agglutination assay by:
   forming a reaction solution containing fixed hemocytes sensitized with anti-HBs monoclonal antibody HBs 22B7;
   adding anti-HBs monoclonal antibody HBs 22B7 denatured by glutaraldehyde to said reaction solution;
   optionally adding denatured and/or undenatured monoclonal antibodies against an antigen other than HBs;
   adding a biological sample; and
   detecting agglutination as a measure of hepatitis.

5. The method of claim 4, wherein two types of fixed hemocytes are used.

6. The method of claim 5, wherein said two types of fixed hemocytes are those sensitized with HBs 8Cl and HBs 22B7 and those sensitized with HBs 18E9 and HBs 22B7.

7. The method of claim 4, wherein said monoclonal antibodies against an antigen other than HBs are undenatured HIgM 10C9 and/or thermally denatured MPV 10G3.

* * * * *